US008835389B2

(12) United States Patent
Azria et al.

(10) Patent No.: US 8,835,389 B2
(45) Date of Patent: Sep. 16, 2014

(54) USE OF CALCITONIN FOR THE TREATMENT OF RA (75) Inventors: Moise Azria, Basel (CH); Claus Christiansen, Ballerup (DK)

(73) Assignees: Novartis AG, Basel (CH); Nordic Bioscience A/S, Herlev (DK)

(*) Notice: Subject to any disclaimer, the term of this patent is extended or adjusted under 35 U.S.C. 154(b) by 402 days.

(21) Appl. No.: 12/091,978

(22) PCT Filed: Nov. 3, 2006

(86) PCT No.: PCT/EP2006/010576
§ 371 (c)(1),
(2), (4) Date: Apr. 29, 2008

(87) PCT Pub. No.: WO2007/051641
PCT Pub. Date: May 10, 2007

(65) Prior Publication Data
US 2008/0226737 A1 Sep. 18, 2008

(30) Foreign Application Priority Data
Nov. 4, 2005 (GB) .................................. 0522566.9

(51) Int. Cl.
*A61K 38/00* (2006.01)
*A61P 19/02* (2006.01)
*A61P 29/00* (2006.01)
*A61K 31/609* (2006.01)
*A61K 38/23* (2006.01)

(52) U.S. Cl.
CPC ............... *A61K 31/609* (2013.01); *A61K 38/23* (2013.01)
USPC ....................................... 514/16.6

(58) Field of Classification Search
None
See application file for complete search history.

(56) References Cited

U.S. PATENT DOCUMENTS

| | | | |
|---|---|---|---|
| 5,912,014 A | 6/1999 | Stern et al. | |
| 7,049,283 B2 * | 5/2006 | Ault et al. | 514/2 |
| 7,184,851 B2 * | 2/2007 | Chang et al. | 700/112 |
| 7,384,982 B2 * | 6/2008 | Bay et al. | 514/563 |
| 7,569,539 B2 | 8/2009 | Azria | |
| 7,749,954 B2 * | 7/2010 | Azria et al. | 514/11.9 |
| 2004/0259952 A1 * | 12/2004 | Abbas et al. | 514/571 |
| 2008/0194676 A1 * | 8/2008 | Abbas et al. | 514/456 |
| 2011/0092426 A1 * | 4/2011 | Arnold et al. | 514/11.9 |
| 2012/0219603 A1 * | 8/2012 | Azria et al. | 424/400 |

FOREIGN PATENT DOCUMENTS

| | | |
|---|---|---|
| JP | A-2005-501852 | 1/2005 |
| WO | 00/59863 | 10/2000 |
| WO | 02/45754 | 6/2002 |
| WO | WO02098453 | 12/2002 |
| WO | 03/076440 | 9/2003 |
| WO | 2004012772 | 2/2004 |
| WO | WO 2005/004900 | 1/2005 |
| WO | 2005/014031 | 2/2005 |

OTHER PUBLICATIONS

Aida. Effects of eel calcitonin on rheumatoid arthritis. Annals of the Rheumatic Diseases. 1991, Vol. 50, pp. 202-203.*
Buclin et al. Bioavailability and Biological Efficacy of a New Oral Formulation of Salmon Calcitonin in Healthy Volunteers. Journal of Bone and Mineral Research. 2002. vol. 17, No. 8, pp. 1478-1485.*
Tanko et al. Safety and Efficacy of a Novel Salmon Calcitonin (sCT) Technology-Based Oral Formulation in Healthy Postmenopausal Women: Acute and 3-Month Effects on Biomarkers of Bone Turnover. 2004, vol. 19, No. 9, pp. 1531-1538.*
Bagger, YZ, "Oral salmon calcitonin induced suppression of urinary collagen type II degradation in postmenopausal women: a new potential treatment of osteoarthritis", *Bone*, Sep. 2005;37(3):425-30.
Kroger H., Effect of calcitonin on bone histomorphometry and bone metabolism in rheumatoid arthritis, *Calcif Tissue Int.* Jan. 1992;50(1):11-3.
Sileghem A., Intranasal calcitonin for the prevention of bone erosion and bone loss in rheumatoid arthritis, *Ann Rheum Dis.* Jun. 1992;51(6):761-4.
Kotaniemi A., Is continuous intranasal salmon calcitonin effective in treating axial bone loss in patients with active rheumatoid arthritis receiving low dose glucocorticoid therapy?, *J Rheumatol.* Nov. 1996;23(11):1875-9.
Farumashia, 1983, vol. 19, No. 2, p. 187-191.
Pain Research, 1990, vol. 5, No. 1, p. 85-91.
The Journal of the Japanese Orthopaedic Association, 2001, vol. 75, No. 2, p. S316, 2-Q-12.
XP008016118 "La calcitonina nell osteoporosi delle malattie reumatiche", Consoli G, et al., La Clinica Terapeutica; 118 p. 37-47 (1992). English summary on p. 45.

* cited by examiner

Primary Examiner — Marcela M Cordero Garcia
(74) Attorney, Agent, or Firm — Ann R. Pokalsky; Dilworth & Barrese, LLP

(57) ABSTRACT

The present invention relates to a novel use of calcitonin in rheumatoid arthritis, and to methods of treating and/or preventing rheumatoid arthritis and conditions associated therewith in mammals, particularly humans. In particular, a method is provided of preventing or/and treating rheumatoid arthritis in a patient in need thereof comprising administering to said patient a therapeutically effective amount of calcitonin, e.g. salmon calcitonin in free form or salt form, in a pharmaceutically acceptable oral delivery form, wherein the therapeutically effective amount of a calcitonin is delivered orally in a composition comprising the calcitonin and a delivery agent for calcitonin.

12 Claims, 2 Drawing Sheets

USE OF CALCITONIN FOR THE TREATMENT OF RA

The present invention relates to a novel use of calcitonin in rheumatoid arthritis, and to methods of treating and/or preventing rheumatoid arthritis in mammals, particularly humans.

Calcitonins, e.g. salmon, (Asu 1-7)-eel or human calcitonin, of the invention are compounds which are long-chain polypeptide hormones secreted by the parafollicular cells of the thyroid gland in mammals and by the ultimobranchial gland of birds and fish. Calcitonin is mainly known as a potent inhibitor of osteoclastic bone resorption, which implicates bone attachment of osteoclasts and enzymatic degradation. Furthermore, it was found that there are effects of Intranasal Salmon Calcitonin in Juvenile Idiopathic Arthritis in humans (Siamopoulou A. et al, 2001, Calcif Tissue Int 69: 25-30) and in the prevention of bone erosion and bone loss in rheumatoid arthritis in humans (Sileghem A., 1992, Annals of Rheumatic Diseases 51: 761-764). The degradative process associates synthesis of various proteases and metalloproteinases, activation of inactive proenymes and inhibition of active enzymes (Leloup G, 1994, J Bone Miner Res, 9, 891-902). Calcitonin is known to induce osteoclast retraction (Zheng M H, et al., 1992, Exper Mole Pathol, 57: 105-115) and to interfere at least with some steps of the enzymatic process of bone resorption (Einhorn T A et al., 1991, Clin Orthop 262: 286-297). There are some reported studies on the effects of calcitonin on articular cartilage. In vitro, calcitonin was found to stimulate proteoglycan and collagen synthesis in animal epiphyseal cartilage (Baxter et al., 1984, Endocrinology 114: 1196-1202) as well as in rabbit and human cartilage (Franchimont P, 1989, J Clin End Metab 69: 259-266).

In accordance with the present invention, it has now surprisingly been found that oral delivery of calcitonin, e.g. salmon, (Asu 1-7)-eel or human calcitonin is useful in the prevention and treatment of rheumatoid arthritis in mammals, particularly humans.

Said oral delivery of calcitonin surprisingly shows better results than other delivery routes and therefore is the delivery route of choice since reliably absorbed, convenient, relatively easy and generally painless, resulting in greater patient compliance relative to other modes of delivery.

Said oral delivery of calcitonin surprisingly shows better absorption and then more suitable pharmacokinetic profile (PK profile) and less variability.

Rheumatoid arthritis (RA), a chronic, systemic, inflammatory autoimmune disease, has as its primary target the synovial tissues. When the disease is unchecked, it leads to substantial disability and premature death. It affects approximately 0.8 percent of adults worldwide, is more common in women (by a ratio of 3 to 1), and has an earlier onset in women, frequently beginning in the childbearing years.

Joint damage occurs early in the course of rheumatoid arthritis; 30 percent of patients have radiographic evidence of bony erosions at the time of diagnosis, and this proportion increases to 60 percent by two years. The diagnosis cannot be established by a single laboratory test or procedure but is aided by the use of seven diagnostic criteria that favor clinical factors and, therefore, depend on the clinician's asking insightful questions and recognizing the often-subtle early physical findings. The diagnostic criteria are the presence of morning stiffness, arthritis of three or more joint areas, arthritis of the hand joints, symmetric arthritis, rheumatoid nodules, elevated levels of serum rheumatoid factor, and radiographic changes. Many other syndromes, including self-limiting viral conditions lasting several weeks, mimic rheumatoid arthritis.

Rheumatoid arthritis is a disease characterised by inflammation and swelling of skeletal joints, especially the small joints of the extremities, leading to erosion and destruction of cartilage and bone. The present invention may be used to inhibit, halt or even reverse the cartilage and bone erosion and destruction, and to decrease the pain, associated with rheumatoid arthritis.

In accordance with the particular findings of the present invention, there is provided:

1.1 A method of preventing or/and treating rheumatoid arthritis in a patient in need thereof comprising administering to said patient a therapeutically effective amount of calcitonin, e.g. salmon calcitonin in free form or salt form, in a pharmaceutically acceptable oral delivery form, wherein the therapeutically effective amount of a calcitonin is delivered orally in a composition comprising the calcitonin and a delivery agent for calcitonin.

1.2 A method of preventing or/and treating rheumatoid arthritis in a patient in need thereof comprising administering to said patient a therapeutically effective amount of calcitonin, e.g. salmon calcitonin in free form or salt form, in a pharmaceutically acceptable oral delivery form, wherein the therapeutically effective amount of a calcitonin is delivered orally in a composition comprising the calcitonin which is conjugated to a polymer molecule.

1.3 A method of inhibiting inflammation of the joints in a patient in need thereof comprising administering orally to said patient a therapeutically effective amount of calcitonin, e.g. salmon calcitonin in free form or salt form, in a pharmaceutically acceptable oral delivery form;

1.4 A method of inhibiting swelling of skeletal joints in a patient in need thereof comprising administering orally to said patient a therapeutically effective amount of calcitonin, e.g. salmon calcitonin in free form or salt form, in a pharmaceutically acceptable oral delivery form;

1.5 A method of inhibiting, halting or even reversing the cartilage and bone erosion and destruction in a patient in need thereof comprising administering orally to said patient a therapeutically effective amount of calcitonin, e.g. salmon calcitonin in free form or salt form, in a pharmaceutically acceptable oral delivery form;

1.6 A method of decreasing pain, associated with rheumatoid arthritis in a patient in need thereof comprising administering orally to said patient a therapeutically effective amount of calcitonin, e.g. salmon calcitonin in free form or salt form, in a pharmaceutically acceptable oral delivery form;

1.7 A method as defined above, comprising co-administration of a therapeutically effective amount of calcitonin, e.g. salmon calcitonin in free form or salt form, in a pharmaceutically acceptable oral delivery form, and a second drug substance.

Suitable second drug substances may include a calcitonin of different origin, e.g. salmon, (Asu 1-7)-eel or human calcitonin, a calcitonin analogue or derivative thereof, COX-2 inhibitors, e.g. lumiracoxib (Prexige®), celecoxib (Celebrex®), rofecoxib (Vioxx®), valdecoxib (Bextra®), etoricoxib (Arcoxia®), or mixed COX-1 and COX-2 inhibitors, e.g. diclofenac, Etanercept, (Enbrel®), pain killers (e.g. Aspirin, Paracetamol), bone formers and bone antiresorbers.

1.8 A method as defined above, comprising co-administration of a therapeutically effective amount of calcitonin, e.g. salmon calcitonin in free form or salt form, in a pharmaceutically acceptable oral delivery form, and a second drug substance, said second drug substance being salmon, (Asu 1-7)-eel or human calcitonin, a calcitonin analogue or derivative thereof in free form or salt form.

1.9 A method as defined above, comprising co-administration of a therapeutically effective amount of calcitonin, e.g. salmon calcitonin in free form or salt form, in a pharmaceutically acceptable oral delivery form, and a second drug substance, said second drug substance being a COX-2 inhibitor e.g. lumiracoxib (Prexige®), celecoxib (Celebrex®), rofecoxib (Vioxx®), valdecoxib (Bextra®), etoricoxib (Arcoxia®), in free form or salt form.

2. A method as defined above, comprising co-administration of a therapeutically effective amount of calcitonin, e.g. salmon calcitonin in free form or salt form, in a pharmaceutically acceptable oral delivery form, and a second drug substance, said second drug substance being a mixed COX-1 and COX-2 inhibitors, e.g. diclofenac in free form or salt form.

2.1 A method as defined above, comprising co-administration of a therapeutically effective amount of calcitonin, e.g. salmon calcitonin in free form or salt form, in a pharmaceutically acceptable oral delivery form, and a second drug substance, said second drug substance being a pain killers (e.g. Aspirin, Paracetamol). in free form or salt form.

2.2 A method as defined above, comprising co-administration of a therapeutically effective amount of calcitonin, e.g. salmon calcitonin in free form or salt form, in a pharmaceutically acceptable oral delivery form, and a second drug substance, said second drug substance being Etanercept, (Enbrel®) in free form or salt form.

Etanercept (Enbrel®) is a dimeric fusion protein consisting of the extracellular legand-binding portion of the human 75 kilodalton tumor necrosis factor receptor (TNFR). It is a anti TNF which binds specifically to TNF receptors and blocks its interaction with cell surface TNF receptors In another aspect, the invention provides a particular dosage range for a calcitonin, e.g. salmon calcitonin, which is efficacious and well tolerated, i.e. safe for a patient to take. Preferred is a range between 0.4 and 2.5 mg of salmon calcitonin for a patient, e.g. human, e.g. an average human of about 70 kg. More preferred are doses around 0.8 mg, e.g. between 0.6 and 1.2 mg. Also preferred are doses less than 1 mg but higher than 0.4 mg. Even more preferred is a dose of about 0.6-0.8 mg, e.g. 0.8 mg. Most preferred is a dose of about 0.8 mg, e.g. between 0.8 and 1.2 mg, administered once per day to a patient in need thereof. Pharmaceutical compositions comprising said doses according to the invention are appropriate for oral delivery. The dosage regimen may be once a day or twice a day, preferably one in the morning and one in the evening.

2.3 A method of preventing or/and treating rheumatoid arthritis in a patient in need thereof comprising administering orally to said patient a pharmaceutical composition comprising between 0.4 and 2.5 mg, preferably between 0.6 and 1.2 mg of a calcitonin, e.g. salmon calcitonin.

2.4 The use of a calcitonin, e.g. salmon calcitonin, in the manufacture of a medicament for the treatment and/or prevention of rheumatoid arthritis, wherein said calcitonin is provided in a pharmaceutical composition administered orally comprising between 0.4 and 2.5 mg, preferably between 0.6 and 1.2 mg of a calcitonin, e.g. salmon calcitonin.

2.5 A pharmaceutical composition for oral use in treating or/and preventing rheumatoid arthritis comprising between 0.4 and 2.5 mg, preferably between 0.6 and 1.2 mg of a calcitonin, e.g. salmon calcitonin.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

As alternative to the above the present invention also provides:

2.6. A calcitonin, e.g. salmon, (Asu 1-7)-eel or human calcitonin in free form or salt form, in a pharmaceutically acceptable oral delivery form, for use in any method as defined under 1.1 to 2.3 above; or 2.7. A calcitonin, e.g. salmon, (Asu 1-7)-eel or human calcitonin in free form or salt form, in a pharmaceutically acceptable oral delivery form, for use in the manufacture of a medicament in any indications as defined under 1.1 to 1.6 above; or 2.8. A pharmaceutical composition for use in any indications as defined under 1.1 to 1.6 above comprising a calcitonin, e.g. salmon, (Asu 1-7)-eel or human calcitonin in free form or salt form, in a pharmaceutically acceptable oral delivery form, together with one or more pharmaceutically acceptable diluents or carriers therefore.

2.9. A pharmaceutical combination comprising:

a) a first agent which is a calcitonin, e.g. salmon, (Asu 1-7)-eel or human calcitonin in free form or salt form, in pharmaceutically acceptable oral delivery form, and b) a co-agent which is selected from the group consisting of salmon, (Asu 1-7)-eel or human calcitonin, a calcitonin analogue or derivative thereof, COX-2 inhibitors, e.g. lumiracoxib (Prexige®), celecoxib (Celebrex®), rofecoxib (Vioxx®), valdecoxib (Bextra®), etoricoxib (Arcoxia®), or mixed COX-1 and COX-2 inhibitors, e.g. diclofenac, Etanercept (Enbrel®), pain killers (e.g. Aspirin, Paracetamol), bone formers and bone antiresorbers. e.g. as disclosed above.

3. A kit of parts for use in the prevention and/or treatment of rheumatoid arthritis, said kit comprising:

a) a first agent which is a calcitonin, e.g. salmon, (Asu 1-7)-eel or human calcitonin in free form or salt form, in pharmaceutically acceptable oral delivery form, and b) a co-agent which is selected from the group consisting of salmon, (Asu 1-7)-eel or human calcitonin, a calcitonin analogue or derivative thereof, COX-2 inhibitors, e.g. lumiracoxib (Prexige®), celecoxib (Celebrex®), rofecoxib (Vioxx®), valdecoxib (Bextra®), etoricoxib (Arcoxia®), or mixed COX-1 and COX-2 inhibitors, e.g. diclofenac, Etanercept (Enbrel®), pain killers (e.g. Aspirin, Paracetamol, bone formers and bone antiresorbers.

In particular, the present invention relates to a method of preventing or treating Rheumatoid arthritis or a condition associated therewith such as inflammation of the joints, swelling of skeletal joints, cartilage and bone erosion and destruction, in a patient in need thereof comprising administering orally to said patient a therapeutically effective amount of a calcitonin, particularly a salmon calcitonin, an (Asu 1-7)-eel or human calcitonin, but more particularly a salmon calcitonin, in free or salt form and a delivery agent for calcitonin.

In one embodiment of the invention, a method is provided for decreasing pain, associated with rheumatoid arthritis in a patient in need thereof comprising administering orally to said patient a therapeutically effective amount of a calcitonin in free or salt form and a delivery agent for calcitonin.

In another embodiment, the invention relates to a method of preventing or treating Rheumatoid arthritis or a condition associated therewith in a patient in need thereof comprising administering orally to said patient a therapeutically effective amount of a calcitonin, particularly a salmon calcitonin, in free or salt form and a delivery agent for calcitonin wherein the delivery agent is a compound of the following formula I Formula I wherein
$R^1$, $R^2$, $R^3$, and $R^4$ are independently hydrogen, —OH, —$NR^6R^7$, halogen, $C_1$-$C_4$alkyl, or $C_1$-$C_4$alkoxy;
$R^5$ is a substituted or unsubstituted $C_2$-$C_{16}$alkylene, substituted or unsubstituted $C_2$-$C_{16}$alkenylene, substituted or unsubstituted $C_1$-$C_{12}$alkyl(arylene), or substituted or unsubstituted aryl($C_1$-$C_{12}$alkylene); and
$R^6$ and $R^7$ are independently hydrogen, oxygen, or $C_1$-$C_4$ alkyl; and a disodium salt, hydrates and alcohol solvates thereof.

In particular, the delivery agent is selected from the group of 5-CNAC, SNAD and SNAC, and their pharmaceutically acceptable salts; but particularly a disodium salt of 5-CNAC, a disodium salt of SNAD, and a disodium salt of SNAC.

In another embodiment, the delivery agent used in the method according to the invention is provided in a micronized form, particularly in a micronized form with an average particle size of less than 40, more particularly of less than 20, and even more particularly of less than 10 micrometers.

In still another embodiment, a method is provided according to the invention, wherein the therapeutically effective amount of a calcitonin is delivered orally in a composition comprising the calcitonin which is conjugated to a polymer molecule.

In a further embodiment, a method is provided according to the invention, wherein the therapeutically effective amount of a calcitonin is delivered in a therapeutically effective unit dosage form comprising calcitonin, at least one pharmaceutically acceptable pH-lowering agent, at least one absorption enhancer, and an enteric coating.

In particular, the invention relates to a method of preventing or treating Rheumatoid arthritis or a condition associated therewith in a patient in need thereof comprising administering orally to said patient a therapeutically effective amount of a calcitonin, particularly a salmon calcitonin, in free or salt form and a delivery agent for calcitonin wherein the therapeutically effective amount of calcitonin is in a dosage range of between 0.4 mg and 2.5 mg for a patient, e.g. human, e.g. an average human of about 70 kg together with a delivery agent for calcitonin. More particularly, doses of around 0.8 mg, e.g. between 0.6 and 1.2 mg may be used in a method according to the invention, even more particularly doses of less than 1 mg but higher than 0.4 mg such as, for example, a dose of about 0.6-0.8 mg, e.g. 0.8 mg, but especially a dose of about 0.8 mg, e.g. between 0.8 and 1.2 mg. Said doses are administered in a single or multiple dosage form, but particularly once per day or, in the alternative, twice a day.

In still a further embodiment, the invention relates to the use of a calcitonin for the manufacture of a medicament for oral administration comprising a therapeutically effective amount of a calcitonin, particularly a salmon calcitonin, an (Asu 1-7)-eel or human calcitonin, but more particularly a salmon calcitonin, in free or salt form and a delivery agent for calcitonin for the prevention or treatment of Rheumatoid arthritis in a patient in need thereof, particularly a delivery agent which is a compound of the following formula I Formula I wherein
$R^1$, $R^2$, $R^3$, and $R^4$ are independently hydrogen, —OH, —$NR^6R^7$, halogen, $C_1$-$C_4$alkyl, or $C_1$-$C_4$alkoxy;
$R^5$ is a substituted or unsubstituted $C_2$-$C_{16}$alkylene, substituted or unsubstituted $C_2$-$C_{16}$alkenylene, substituted or unsubstituted $C_1$-$C_{12}$alkyl(arylene), or substituted or unsubstituted aryl($C_1$-$C_{12}$alkylene); and
$R^6$ and $R^7$ are independently hydrogen, oxygen, or $C_1$-$C_4$ alkyl; and a disodium salt, hydrates and alcohol solvates thereof.

In particular, the delivery agent is selected from the group of 5-CNAC, SNAD and SNAC, and their pharmaceutically acceptable salts; but particularly a disodium salt of 5-CNAC, a disodium salt of SNAD, and a disodium salt of SNAC.

In another embodiment of the invention, the delivery agent according to the invention is provided in a micronized form, particularly with an average particle size of less than 40, more particularly of less than 20, and even more particularly of less than 10 micrometers.

In another embodiment of the invention, the calcitonin is used in conjugation with a polymer molecule.

In still another embodiment, the calcitonin is used together with at least one pharmaceutically acceptable pH-lowering agent, at least one absorption enhancer, and an enteric coating.

In particular, the calcitonin is used in a therapeutically effective amount in free or salt form in a dosage range of between 0.4 mg and 2.5 mg for a patient, e.g. human, e.g. an average human of about 70 kg together with a delivery agent for calcitonin. More particularly, doses of around 0.8 mg, e.g. between 0.6 and 1.2 mg may be used in a method according to the invention, even more particularly doses of less than 1 mg but higher than 0.4 mg such as, for example, a dose of about 0.6-0.8 mg, e.g. 0.8 mg, but especially a dose of about 0.8 mg, e.g. between 0.8 and 1.2 mg. Said doses are administered in a single or multiple dosage form, but particularly once per day or, in the alternative, twice a day.

In still another embodiment of the invention, a pharmaceutical composition for use in the oral treatment or prevention of Rheumatoid arthritis, or of a condition associated therewith, in a patient in need thereof is provided, comprising a calcitonin, particularly a salmon calcitonin, an (Asu 1-7)-eel or human calcitonin, but more particularly a salmon calcitonin, in free or salt form and a delivery agent for calcitonin together with one or more pharmaceutically acceptable diluents or carriers therefore.

In particular, the invention relates to a pharmaceutical composition according to the invention and as disclosed herein before, wherein the delivery agent is a compound of the following formula I Formula I wherein
R¹, R², R³, and R⁴ are independently hydrogen, —OH, —NR⁶R⁷, halogen, $C_1$-$C_4$alkyl, or $C_1$-$C_4$alkoxy;
R⁵ is a substituted or unsubstituted $C_2$-$C_{16}$alkylene, substituted or unsubstituted $C_2$-$C_{16}$alkenylene, substituted or unsubstituted $C_1$-$C_{12}$alkyl(arylene), or substituted or unsubstituted aryl($C_1$-$C_{12}$alkylene); and
R⁶ and R⁷ are independently hydrogen, oxygen, or $C_1$-$C_4$ alkyl; and a disodium salt, hydrates and alcohol solvates thereof.

More particularly, the invention relates to a pharmaceutical composition according to the invention and as disclosed herein before, wherein the delivery agent is selected from the group of 5-CNAC, SNAD and SNAC, and their pharmaceutically acceptable salts; but particularly a disodium salt of 5-CNAC, a disodium salt of SNAD, and a disodium salt of SNAC.

In another embodiment, the delivery agent used in the method according to the invention is provided in a micronized form, particularly in a micronized form with an average particle size of less than 40, more particularly of less than 20, and even more particularly of less than 10 micrometers.

In still another embodiment the invention relates to a pharmaceutical composition for oral delivery according to the invention comprising calcitonin in a therapeutically effective amount which is conjugated to a polymer molecule.

In still another embodiment the invention relates to a pharmaceutical composition according to the invention, comprising a therapeutically effective amount of a calcitonin and at least one pharmaceutically acceptable pH-lowering agent, at least one absorption enhancer, and an enteric coating.

In another embodiment of the invention, a pharmaceutical composition is provided for preventing or treating Rheumatoid arthritis, or a condition associated therewith, in a patient in need thereof comprising a therapeutically effective amount of a calcitonin in free or salt form in a dosage range of between 0.4 mg and 2.5 mg together with a delivery agent for calcitonin. More particularly, the pharmaceutical composition comprises calcitonin in a dosis range of around 0.8 mg, e.g. between 0.6 and 1.2 mg, even more particularly of less than 1 mg but higher than 0.4 mg such as, for example, a dosis range of about 0.6-0.8 mg, e.g. 0.8 mg, but especially a dosis range of about 0.8 mg, e.g. between 0.8 and 1.2 mg. Said doses are administered in a single or multiple dosage form, but particularly once per day or, in the alternative, twice a day.

In still another embodiment, the invention provides a pharmaceutical combination for use in the oral treatment or prevention of Rheumatoid arthritis in a patient in need thereof, comprising:
a. a first agent which is a calcitonin, particularly a salmon calcitonin, an (Asu 1-7)-eel or human calcitonin, more particularly a salmon calcitonin, which calcitonin is present in a dosis range of between 0.4 and 2.5 mg, and
b. a co-agent which is selected from the group consisting of salmon, (Asu 1-7)-eel or human calcitonin; a calcitonin analogue or derivative thereof; COX-2 inhibitors, e.g. lumiracoxib (Prexige®), celecoxib (Celebrex®), rofecoxib (Vioxx®), valdecoxib (Bextra®), etoricoxib (Arcoxia®); or mixed COX-1 and COX-2 inhibitors, e.g. diclofenac; Etanercept (Enbrel®); pain killers (e.g. Aspirin, Paracetamol); bone Formers and bone antiresorbers.

The term "oral" as used herein comprises any kind of oral delivery routes (comprising buccal and sublingual routes).

"Delivery agent" as used herein refers to carrier compounds or carrier molecules that are useful in the oral delivery of therapeutic agents. "Delivery agent" may be used herein interchangeably with "carrier".

By a "Therapeutically effective amount" of calcitonin as provided in the oral dosage forms according to the present invention is to be understood as an amount of calcitonin which is sufficient to achieve a clinically significant improvement of a condition associated with Rheumatoid arthritis in a human or animal patient such as, for example, inhibition of inflammation of the joints or the of the swelling of skeletal joints, inhibition, halting and/or reversion of cartilage and bone erosion and destruction, and/or decrease of pain or which is sufficient to prevent the onset of said conditions.

The term "patient" as used herein means a patient in need of being treated or prevented from rheumatoid arthritis or any method as defined under 1.1 to 2.3 above, whereas patient means mammals, such as rodents, cows, pigs, dogs, cats, and primates, particularly humans.

The term "pharmaceutical combination" as used herein means a product that results from the mixing or combining of more than one active ingredient and includes both fixed and non-fixed combinations of the active ingredients.

The term "fixed combination" means that the active ingredients, e.g. salmon calcitonin and a co-agent, are both administered to a patient simultaneously in the form of a single entity or dosage.

The term "non-fixed combination" means that the active ingredients, e.g. salmon calcitonin and a co-agent, are both administered to a patient as separate entities either simultaneously, concurrently or sequentially with no specific time limits, wherein such administration provides therapeutically effective levels of the 2 compounds in the body of the patient.

"Oral Unit-Dose Form" refers to physically discrete units suitable for human and animal consumption and packaged individually as is known in the art. It is contemplated for purposes of the present invention that dosage forms of the present invention comprising therapeutically effective amounts of calcitonin and a delivery agent may include one or more unit doses (e.g., tablets, capsules) to achieve the therapeutic effect.

The term "multiple dose" means that pharmaceutical composition according to the invention comprising therapeutically effective amounts of calcitonin and a delivery agent, particularly in form of a oral unit dose will be administered to a human or animal patient in at least two doses in accordance with the dosing interval appropriate for that composition.

The term "single dose" means that the pharmaceutical composition according to the invention comprising therapeutically effective amounts of calcitonin and a delivery agent, particularly in form of a oral unit dose will be administered to a human or animal patient in a single dose.

Preferably the calcitonin, e.g. salmon calcitonin in free form or in pharmaceutically acceptable salt form, is co-administered with a protease inhibitor, e.g. cathepsin inhibitor, e.g. cathepsin K inhibitor.

Utility of calcitonin, e.g. salmon calcitonin in free form or salt form, in pharmaceutically acceptable oral delivery form for use in any method as defined under 1.1 to 1.10 or in any pharmaceutical composition as disclosed herein before, may be demonstrated in animal test methods as well as in clinic.

In an embodiment of the invention, a pharmaceutical composition for use in the oral treatment or prevention of Rheumatoid arthritis, or of a condition associated therewith, in a patient in need thereof is provided, comprising a calcitonin, particularly a salmon calcitonin, in free or salt form and a delivery agent for calcitonin, and, optionally, a conventional pharmaceutically acceptable excipient.

The calcitonin can be any calcitonin, including natural, synthetic or recombinant sources thereof, as well as calcitonin derivatives such as 1,7-Asu-eel calcitonin. The compositions can comprise a single calcitonin or any combination of two or more calcitonins. The preferred calcitonin is synthetic salmon calcitonin.

Various calcitonins, including salmon, pig and eel calcitonin are commercially available or may be synthesized by known methods.

Dosage forms for oral administration include tablets, capsules, lozenges, pills, wafers, granules, oral liquids such as syrups, suspensions, solutions, emulsions, powder for reconstitution.

For the purpose of the present invention, a therapeutically effective dosage will generally be from about 0.4 mg/day to about 2.5 mg/day, particularly from about 0.6 mg/day to about 1.2 mg/day, and more particularly from about 0.6 mg/day to about 0.8 mg/day or form about 0.8 mg/day to about 1.2 mg/day, which may be administered in one or multiple doses, particularly once or twice a day to a patient, e.g. a human, e.g. an average human of about 70 kg.

When the pharmacologically active agent is salmon calcitonin, the appropriate dosage will, of course, vary depending upon, for example, the host and the nature and severity of the condition being treated. In particular, the specific dose level of the compounds of the invention for any particular patient will depend on a variety of factors such as age, sex, body weight, general health condition, diet, individual response of the patient to be treated time of administration, severity of the disease to be treated, the activity of particular compound applied, dosage form, mode of application and concomitant medication. The therapeutically effective amount for a given situation will readily be determined by routine experimentation and is within the skills and judgment of the ordinary clinician or physician.

However, in general, satisfactory results will be obtained systemically at daily dosages of from about 0.5 µg/kg to about 10 µg/kg animal body weight, preferably 1 µg/kg to about 6 µg/kg body weight. For an average human of about 70 kg this translates into a daily dosage of from about 0.035 to 0.7 mg, particularly from about 0.07 mg to about 0.42 mg.

In another embodiment of the invention, a therapeutically effective dosage of calcitonin will generally be from about 0.035 mg/day to 0.7 mg/day, particularly from about 0.07 mg/day to about 0.42 mg/day; but especially from about 0.42 mg/day to about 0.7 mg/day.

The pharmaceutically acceptable inactive excipients which are used in the oral formulation of calcitonin, may include polymers and inactive compounds which for example, aid the formulation or manufacturing of the solid oral dosage form contemplated by the present invention or which may aid the release of the solid oral composition in the gastro-intestinal environment. The pharmaceutically inactive ingredients, referred to above, for example optionally include crospovidones and povidones, which may be any crospovidone and povidone. Crospovidone is a synthetic crosslinked homopolymer of N-vinyl-2-pyrrolidone, also called 1-ethenyl-2-pyrrolidinone, having a molecular weight of 1,000,000 or more. Commercially available crospovidones include Polyplasdone XL, Polyplasdone XL-10, Polyplasdone INF-10 available from ISP, Kollidon CL, available from BASF Corporation. The preferred crospovidone is Polyplasdone XL. Povidone is a synthetic polymer consisting of linear 1-vinyl-2-pyrrolidinone groups having a molecular weight generally between 2,500 and 3,000,000. Commercially available povidones include Kollidon K-30, Kollidon K-90F available from BASF Corporation and Plasdone K-30 and Plasdone K-29/32, available from ISP. As mentioned above, the crospovidones and povidones are commercially available. Alternatively, they may be synthesized by known processes. The crospovidone, povidone or combination thereof is generally present in the compositions in an amount of from 0.02 to 50 percent by weight, particularly in an amount of from 0.5 to 50 percent by weight relative to the total weight of the overall pharmaceutical composition, preferably an amount of from 2 to 25 percent, more preferably 5 to 20 percent by weight, but especially of from 3 to 7 percent by weight relative to the total weight of the pharmaceutical composition.

The delivery agents useful in the formulation, e.g. the oral formulation, are any agents useful for delivering the particular pharmacologically active agent. Suitable delivery agents are any one of the modified amino acids disclosed in aforementioned U.S. Pat. No. 5,866,536 or any one of the modified amino acids described in the aforementioned U.S. Pat. No. 5,773,647 or any combination thereof. The contents of the aforementioned U.S. Pat. Nos. 5,773,647 and 5,866,536 are hereby incorporated by reference in their entirety. In addition, the delivery agent can be the disodium salt of any of the aforementioned modified amino acids as well as ethanol solvates and hydrates thereof. Suitable compounds include compounds of the following formula I Formula I wherein $R^1$, $R^2$, $R^3$, and $R^4$ are independently hydrogen, —OH, —$NR^6R^7$, halogen, $C_1$-$C_4$alkyl, or $C_1$-$C_4$alkoxy;

$R^5$ is a substituted or unsubstituted $C_2$-$C_{16}$alkylene, substituted or unsubstituted $C_2$-$C_{16}$alkenylene, substituted or unsubstituted $C_1$-$C_{12}$alkyl(arylene), or substituted or unsubstituted aryl($C_1$-$C_{12}$alkylene); and $R^6$ and $R^7$ are independently hydrogen, oxygen, or $C_1$-$C_4$ alkyl; and hydrates and alcohol solvates thereof. The compounds of formula I as well as their disodium salts and alcohol solvates and hydrates thereof are described in WO 00/059863, along with methods for preparing them.

The disodium salt may be prepared from the ethanol solvate by evaporating or drying the ethanol solvate by methods known in the art to form the anhydrous disodium salt. Drying is generally carried out at a temperature of from about 80 to about 120° C., preferably from about 85 to about 90° C., and most preferably at about 85° C. The drying step is generally performed at a pressure of 26" Hg or greater. The anhydrous disodium salt generally contains less than about 5% by weight of ethanol and preferably less than about 2% by weight of ethanol, based on 100% total weight of anhydrous disodium salt. The disodium salt of the delivery agent can also be prepared by making a slurry of the delivery agent in water and adding two molar equivalents of aqueous sodium hydroxide, sodium alkoxide or the like. Suitable sodium alkoxides include, but are not limited to, sodium methoxide, sodium ethoxide, and combinations thereof. A still further method of preparing the disodium salt is by reacting the delivery agent with one molar equivalent of sodium hydroxide to yield the disodium salt. The disodium salt can be isolated as a solid by concentrating the solution containing the disodium salt to a thick paste by vacuum distillation. This paste may be dried in a vacuum oven to obtain the disodium salt of the delivery agent as a solid. The solid can also be isolated by spray drying an aqueous solution of the disodium salt. The delivery agents may be prepared by methods known in the art, e.g., as mentioned above, by methods described in U.S. Pat. Nos. 5,773,647 and 5,866,536. The ethanol solvates, as described in the aforementioned WO 00/059863, include, but are not limited to, a molecular or ionic complex of molecules or ions of ethanol solvent with molecules or ions of the disodium salt of the delivery agent. Typically, the ethanol solvate contains about one ethanol molecule or ion for every molecule of disodium salt of the delivery agent. The ethanol solvate of the disodium salt of the delivery agent can be prepared by dissolving the delivery agent in ethanol. Typically, each gram of delivery agent is dissolved in from about 1 to about 50 mL of ethanol and generally, from about 2 to about 10 mL of ethanol. The delivery agent/ethanol solution is then reacted with a molar excess of a sodium containing salt, such as a monosodium containing salt, relative to delivery agent, i.e. for every mole of delivery agent there is more than one mole of sodium cations, yielding the ethanol solvate. Suitable monosodium salts include, but are not limited to, sodium hydroxide; sodium alkoxides, such as sodium methoxide and sodium ethoxide; and any combination of the foregoing. Preferably, at least about two molar equivalents of the monosodium containing salt are added to the ethanol solution, i.e. for every mole of delivery agent there is at least about two moles of sodium cations. Generally, the reaction is performed at or below the reflux temperature of the mixture, such as at ambient temperature. The ethanol solvate is then recovered by methods known is the art, such as, concentration of the resulting slurry at atmospheric distillation, cooling the concentrated slurry and filtering the solid. The recovered solid can then be vacuum dried to obtain the ethanol solvate. The hydrates of the disodium salts of the delivery agents may be prepared by drying the ethanol solvate to from an anhydrous disodium salt, as described above, and hydrating the anhydrous disodium salt. Preferably, the monohydrate of the disodium salt is formed. Since the anhydrous disodium salt is very hydroscopic, the hydrate forms upon exposure to atmospheric moisture. Generally, the hydrating step is performed at from about ambient temperature to about 50° C., preferably ambient temperature to about 30° C. and in an environment having at least 50% relative humidity. Alternatively, the anhydrous disodium salt may be hydrated with steam.

The preferred delivery agents are N-(5-chlorosalicyloyl)-8-aminocaprylic acid (5-CNAC), N-(10-[2-hydroxybenzoyl]amino)decanoic acid (SNAD), N-(8-[2-hydroxybenzoyl]amino)caprylic acid (SNAC) and their pharmaceutically acceptable salts, preferably their monosodium and disodium salts, ethanol solvates of their sodium salts and the monohydrates of their sodium salts and any combinations thereof.

The most preferred delivery agent is the disodium salt of 5-CNAC and the monohydrate thereof. Preferably the disodium salt is present in amount of more than 90% weight per total weight of the 5-CNAC present in the composition.

The active ingredient to delivery agent ratio is particularly present between 1/25 to 1/600, more particularly between 1/25 to 1/400, even more particularly between 1/200 and 1/300 and 1/400 and 1/600, respectively, with the most preferred ratio in the case sCT/5-CNAC compositions being of 0.5 mg-1 mg sCT to 200 mg-300 mg of 5-CNAC disodium salt.

The delivery agent, 5 CNAC, SNAD, and SNAC are very water soluble and nearly fully, i.e. greater than 90%, absorbed by the gastro-intestinal tract whether it is ingested in micronized or coarse form. However, it has been found, surprisingly, that when a micronized form of one of these carrier agents is employed in the composition, the absorption of the pharmacologically active agent of the present composition is more completely absorbed into the blood stream. A micronized form of the carrier agent, which is utilized in preparation of the solid oral dosage form of the present invention, is defined as a carrier agent which, when added to the present composition mixture of pharmacologically active agent and pharmaceutically inactive ingredients, has an average particle size of less than 40 micrometers. Desirably the carrier agent of the present invention has a micronized form which is defined as an average particle size of less than 20 microns. More interestingly, the carrier agent for the present invention has a micronized form which is defined as an average particle size of less than 10 microns. Micronized forms of the carrier agent of the present invention may be prepared by grinding it in a grinding mill which is acceptable for grinding pharmaceutical ingredients and which is capable of grinding the pharmaceutical ingredients and/or carrier agent to a fine and uniform micronized particle size. An example of such a grinding mill is an Air Jet Mill Gem T® (Copley Scientific, Ltd., Nottingham, UK). The finely ground carrier agent either separately or finely ground carrier agent plus any combination of finely ground additional ingredients of the present invention may then be screened, for example, over a mesh screen having the appropriate openings, in order to allow only those ingredients which have the required particle size to pass through and be collected for use in the present invention. The pharmaceutical compositions of the present invention typically contain a delivery effective amount of one or more of the delivery agents, i.e. an amount sufficient to deliver the active agent for the desired effect. Generally, the delivery agent is present in an amount of 2.5% to 99.4% by weight, more preferably 25% to 50% by weight.

Preferably a calcitonin, e.g. salmon calcitonin in free form or in salt form, is delivered as an oral pharmaceutical composition comprising calcitonin and a delivery agent for calcitonin. More preferably said oral pharmaceutical composition comprises a delivery agent selected from the group of 5-CNAC, SNAD, and SNAC. More preferably said oral pharmaceutical composition comprises a delivery agent is selected from the group consisting of a disodium salt of 5-CNAC, a disodium salt of SNAD, and a disodium salt of SNAC. More preferably, said oral pharmaceutical composition comprises a delivery agent in micronized form.

The pharmaceutically acceptable oral delivery form of the composition according to the invention may further comprise a diluent.

The diluent may be, for example Avicel PH 102 or 101. The diluent may be present in the pharmaceutical composition of up to 90 wt % based on the whole composition, or may be used to make up any difference between the desired and actual final pharmaceutical composition mass, which may be, for example up to 600 mg, e.g. 500 mg. Preferably, the binder is present in an amount of between 20 and 70 wt % based on the whole composition, e.g. 40 to 60 wt %, e.g. 50 wt %. Where the final pharmaceutical composition weight is 500 mg, this equates to amounts of, for example, 100 mg to 350 mg.

In a preferred embodiment of the present invention, the diluent is a microcrystalline cellulose.

Alternatively, calcitonin can be orally delivered also with other technologies such as the one described in WO 94/26778; U.S. Pat. No. 5,359,030; U.S. Pat. No. 5,438,040; U.S. Pat. No. 5,681,811; U.S. Pat. No. 6,191,105; U.S. Pat. No. 6,309,633; U.S. Pat. No. 6,380,405; U.S. Pat. No. 6,436,990; U.S. Pat. No. 6,458,776; and U.S. Pat. No. 6,479,692 (the content thereof is hereby incorporated by reference in its entirety). In short, such oral formulations relate generally to conjugation-stabilized (poly)peptide and protein compositions.

More particularly, such oral delivery forms relate in one broad compositional aspect to covalently conjugated calcitonin complexes wherein the calcitonin is covalently bonded to one or more molecules of a polymer incorporating as an integral part thereof a hydrophilic moiety, e.g., a linear polyalkylene glycol, and wherein said polymer incorporates a lipophilic moiety as an integral part thereof. In one particular aspect, such oral delivery forms relate to a physiologically active calcitonin composition comprising a physiologically active peptide covalently coupled with a polymer comprising (i) a linear polyalkylene glycol moiety and (ii) a lipophilic moiety, wherein the peptide, linear polyalkylene glycol moiety, and the lipophilic moiety are conformationally arranged in relation to one another such that the physiologically active peptide in the physiologically active calcitonin composition has an enhanced in vivo resistance to enzymatic degradation, relative to the physiologically active calcitonin alone (i.e., in an unconjugated form devoid of the polymer coupled thereto). In another aspect, such oral delivery forms relate to a physiologically active calcitonin composition of three-dimensional conformation comprising a physiologically active calcitonin covalently coupled with a polysorbate complex comprising (i) a linear polyalkylene glycol moiety and (ii) a lipophilic moiety, wherein the physiologically active calcitonin, the linear polyalkylene glycol moiety and the lipophilic moiety are conformationally arranged in relation to one another such that (a) the lipophilic moiety is exteriorly available in the three-dimensional conformation, and (b) the physiologically active calcitonin in the physiologically active calcitonin composition has an enhanced in vivo resistance to enzymatic degradation, relative to the physiologically active calcitonin alone. In a further aspect, such oral delivery forms relate to a multiligand conjugated calcitonin complex comprising a triglyceride backbone moiety, having: a bioactive calcitonin covalently coupled with the triglyceride backbone moiety through a polyalkylene glycol spacer group bonded at a carbon atom of the triglyceride backbone moiety; and at least one fatty acid moiety covalently attached either directly to a carbon atom of the triglyceride backbone moiety or covalently joined through a polyalkylene glycol spacer moiety. In such multi ligand conjugated calcitonin complex, the d and B carbon atoms of the triglyceride bioactive moiety may have fatty acid moieties attached by covalently bonding either directly thereto, or indirectly covalently bonded thereto through polyalkylene glycol spacer moieties. Alternatively, a fatty acid moiety may be covalently attached either directly or through a polyalkylene glycol spacer moiety to the a and d carbons of the triglyceride backbone moiety, with the bioactive calcitonin being covalently coupled with the 13-carbon of the triglyceride backbone moiety, either being directly covalently bonded thereto or indirectly bonded thereto through a polyalkylene spacer moiety. In such a multiligand conjugated calcitonin complex, the bioactive calcitonin may advantageously be covalently coupled with the triglyceride modified backbone moiety through alkyl spacer groups, or alternatively other acceptable spacer groups, within the broad scope of the invention. As used in such context, acceptability of the spacer group refers to steric, compositional, and end use application specific acceptability characteristics. In yet another aspect such oral delivery forms relate to a polysorbate complex comprising a polysorbate moiety including a triglyceride backbone and functionalizing groups including: (i) a fatty acid group; and (ii) a polyethylene glycol group having a physiologically active moiety covalently bonded thereto, e.g., a physiologically active moiety is covalently bonded to an appropriate functionality of the polyethylene glycol group.

Such covalent bonding may be either direct, e.g., to a hydroxy terminal functionality of the polyethylene glycol group, or alternatively, the covalent bonding may be indirect, e.g., by reactively capping the hydroxy terminus of the polyethylene glycol group with a terminal carboxy functionality spacer group, so that the resulting capped polyethylene glycol group has a terminal carboxy functionality to which the physiologically active moiety may be covalently bonded. Such oral delivery forms relate to a further aspect to a stable, aqueously soluble, conjugated calcitonin complex comprising a physiologically active calcitonin covalently coupled to a physiologically compatible polyethylene glycol modified glycolipid moiety. In such complex, the physiologically active calcitonin may be covalently coupled to the physiologically compatible polyethylene glycol modified glycolipid moiety by a labile covalent bond at a tee amino acid group of the polypeptide. The physiologically compatible polyethylene glycol modified glycolipid moiety may advantageously comprise a polysorbate polymer, e.g., a polysorbate polymer comprising fatty acid ester groups selected from the group consisting of monopalmitate, dipalmitate, monolaurate, dilaurate, trilaurate, monoleate, dioleate, trioleate, monostearate, distearate, and tristearate. In such complex, the physiologically compatible polyethylene glycol modified glycolipid moiety may suitably comprise a polymer selected from the group consisting of polyethylene glycol ethers of fatty acids, and polyethylene glycol esters of fatty acids, wherein the fatty acids for example comprise a fatty acid selected from the group consisting of lauric, palmitic, oleic, and stearic acids. In the above complex, the physiologically active calcitonin may by way of illustration comprise a calcitonin selected from the group consisting of insulin, calcitonin, ACTH, glucagon, somatostatin, somatotropin, somatomedin, parathyroid hormone, erythropoietin, hypothalmic releasing factors, prolactin, thyroid stimulating hormones, endorphins, enkephalins, vasopressin, non-naturally occurring opiods, superoxide dismutase, interferon, asparaginase, arginase, arginine deaminease, adenosine deaminase ribonuclease, trypsin, chemotrypsin, and papain. In another aspect, the present invention relates to an oral administration dosage form for the mediation of insulin deficiency, comprising a pharmaceutically acceptable carrier and a stable, aqueously soluble, conjugated insulin complex comprising insulin or proinsulin covalently coupled to a physiologically compatible polyethylene glycol modified glycolipid moiety.

Furthermore, a further second alternative oral delivery dosage form which may be used according to the invention is a technology described in WO 97/33531; U.S. Pat. No. 5,912,014 and U.S. Pat. No. 608,618 (the content thereof is hereby incorporated by reference in its entirety). In short, such further oral delivery form protects calcitonin from the acidic environment and digestive enzymes as it passes through the stomach and intestine, and facilitates its entry into the bloodstream. Once it is safely in the bloodstream, calcitonin can exert its therapeutic effect. Such oral delivery form is e.g. a pharmaceutical composition for oral delivery of salmon calcitonin comprising: (A) a therapeutically effective amount of said salmon calcitonin; (B) at least one pharmaceutically acceptable pH-lowering agent; (C) at least one absorption enhancer effective to promote bioavailability of said salmon calcitonin; and (D) an enteric coating; wherein said pH-lowering agent is present in said pharmaceutical composition in a quantity which, if added to 10 milliliters of 0.1M aqueous sodium bicarbonate solutions would be sufficient to lower the pH of said solution to no higher than 5.5. The pharmaceutical composition, wherein said enteric coating is present at a weight which is no more than 20% of the weight of the remainder of said pharmaceutical composition excluding said enteric coating. The pharmaceutical composition of above, wherein said enteric coating is present at a weight which is no more than 5-15% of the weight of the remainder of said pharmaceutical composition excluding said enteric coating.

The oral pharmaceutical compositions with which the usefulness of calcitonin in the treatment of rheumatoid arthritis is shown, may be provided as a capsule including a soft-gel capsule, tablet, caplet, other solid oral dosage form, all of which can be prepared by methods well known in the art.

The solid pharmaceutical compositions of the instant invention can be prepared by first grinding either the carrier agent or the carrier agent with any combination of the additional ingredients of the present composition to a micronized particle size. The micronized carrier agent or micronized carrier agent plus micronized additional ingredients of the present invention may then be further processed by conventional methods e.g. by blending a mixture of the active agent or active agents, the delivery agent, the crospovidone or povidone and other ingredients, kneading, and filling into capsules or, instead of filling into capsules, molding followed by further tableting or compression-molding to give tablets. In addition, a solid dispersion may be formed by known methods followed by further processing to form a tablet or capsule.

The following examples serve to further illustrate the invention and will be readily understood by one of ordinary skill in the art. The examples are not meant to be limiting of the present invention in any way.

EXAMPLES

A. Formulation Examples

Example 1

Formulation 1 (3 batches)

Preparation of Micronized 5-CNAC: Coarse 5-CNAC, which is to be micronized, is added to a jet mill (Air Jet Mill Gem T® Copley Scientific, Ltd., Nottingham, UK) using a 80 ceramic pan cake jet mill, 8 cm diameter, 6 bar N2, 0.5 mm nozzles with manual feed of about 700 g/h. The coarse 5-CNAC is jet milled and periodically sampled under microscope with reference ruler measurements to identify when the average desired micronized particle size is obtained. Three different batches are ground to create a mean particle size, i.e. D50=6 um, 35 um, and 46 um batches. Individual sieving of the separate micronized batches is then done by using a conical sieve mill (Quadro Comil, Quadro Engineering Incorporated 613 Colby Drive, Waterloo, Ontario, Canada N2V 1A1) with a U10, 813 um conical sieve, round beater, operating at 1500 rpm with throughput of about 150 kg/h.

Formulation 1-3. Salmon Calcitonin Formulation with 5-CNAC of Different Particle Size

| Ingredient | Amount (mg) | Percent (%) |
| --- | --- | --- |
| Salmon Calcitonin | 1 | 0.25 |
| Micronized 5-CNAC | 228 | 57 |
| Avicel PH 102 ® | 147 | 36.75 |
| Crospovidone, NF | 20 | 5 |
| Magnesium stearate | 4 | 1 |
| Total | 400 | 100 |

Preparation of Formulation 1: Three different batches of tablets are prepared using the three different batches of micronized 5-CNAC disodium, one tablet batch having an average 5-CNAC disodium particle size of 46 microns (Batch A), a second tablet batch having an average 5-CNAC disodium particle size of 6 microns (Batch B), and a third tablet batch having an average 5-CNAC disodium particle size of 35 microns (Batch C).

0.50 g of salmon calcitonin, pre-screened through a 40 mesh screen, 57. g of micronized 5-CNAC disodium salt, screened through a 35 mesh screen, and 10 g of Polyplasdone XL (crospovidone, NF, International Specialty Products, 1361 Alps Road, Wayne, N.J., 07470, USA) is combined in a 500 mL jar and is mixed using a Turbula mixer for 100 revolutions at a speed of 46 RPM. An additional 57. g of micronized 5-CNAC disodium salt, screened through a 35 mesh screen, and 36.75 g of Avicel PH 102® is added to the jar and mixed for 500 revolutions at a speed of 46 RPM. A further 36.75 g of Avicel PH 102® is added to the jar and is mixed for an additional 100 revolutions at a speed of 46 RPM. 2.0 g of magnesium stearate is screened into the jar using a 35 mesh screen and is blended for 1 minute at a speed of 46 RPM. The final blend is compressed into tablets using a Manesty B3B tablet press. The tablet weight is approximately 400 mg.

Example 2

Preparation of Formulations 2-3

Alternatively, there are further formulations provided:

Formulation 2:

| Ingredient | % for batch | Batch mg per tablet |
| --- | --- | --- |
| Recombinant Salmon calcitonin | 0.12 | 0.6 |
| 5-CNAC (I) | 0.24a | 1.2 |
| 5-CNAC (II) | 45.36b | 226.8 |
| Avicel PH 101 (I) | 3a | 15a |
| Avicel PH 101 (II) | 44.9b | 224.9b |
| Crospovidone | 5 | 25 |
| Aerosil 200 PH | 0.3 | 1.5 |
| Magnesium stearate | 1.0 | 5 |
| Total tablet weight (mg) | 100 | 500 |

Unit weight (a + b) listed as 5-CNAC disodium salt, corresponding to combined weight of 200 mg 5-CNAC free acid.
Unit weight (a + b) of Avicel PH 101 (I) and (II) corresponds to combined weight of Avicel PH 101.

Formulation 3

| Ingredient | % for batch | Batch mg per tablet |
| --- | --- | --- |
| Recombinant Salmon calcitonin | 0.16 | 0.8 |
| 5-CNAC (I) | 2.1a | 4.8a |
| 5-CNAC (II) | 2.1b | 4.8b |
| 5-CNAC (III) | 41.4c | 218.4c |
| Avicel PH 101 (I) | 3a | 15a |
| Avicel PH 101 (II) | 44.9b | 224.7b |
| Crospovidone | 5 | 25 |
| Aerosil 200 PH | 0.3 | 1.5 |
| Magnesium stearate | 1.0 | 5 |
| Total tablet weight (mg) | 100 | 500 |

Unit weight (a + b + c) listed as 5-CNAC disodium salt, corresponding to combined weight of 200 mg 5-CNAC free acid.
Unit weight (a + b) of Avicel PH 101 (I) and (II) corresponds to combined weight of Avicel PH 101.

The process for preparation of the above formulations are similar to that of the one, described in Example 1. However, there is some deviation which are described below:

Step 1: Blend for 50 revolutions

Step 2: Sieve the material together through 0.25 mm screen (60 mesh). Rinse the screen with 5-CNAC (II)

Step 3: Place ingredients into a diffusion blender and blend at for 150 rev

Step 4: Sieve the blended material through 0.85 mm screen (20 mesh)

Step 5: Blend the sieved material for 50 or 100 or 150 rev

Step 6: Compression

1. Weight 0.25 g of sCT DS;
2. Blend with Part I of 5-CNAC;
3. Sieve blended material from Step 2 through #60 (0.25 mm) screen;
4. Rinse the screen from Step 3 with Part II of 5-CNAC;
5. Sieve Aerosil 200PH and Part I of Avicel PH101 through #20 (0.85 mm) mesh screen;
6. Add Avicel PH101 (Part II), sieved material from Step 5, 5-CNAC (Part III), sieved material from Step 4, Crospovidone into diffusion blender and blend for 150 revolutions;
7. Sieve the blended material through #20 mesh (0.85 mm) screen;
8. Sieve Mg Stearate through #20 mesh (0.85 mm) screen and add to blend from Step 7;
9. Lubrication for 50 revolutions
10. Compress the blend into 12 mm round FFBE tablets with NVR/984 embossing.

All the equipments used are the same as described in Example 1.

Example 3

Preparation of Formulation 4

The above mentioned formulation 2 is compressed into tablets with various hardness using Manesty Beta press or Fette 3090 using different compression forces. Resultant tablets having different dissolution profiles were tested in Rhesus Monkeys for oral absorption of sCT. Tablets and their physical properties are listed in Table 1 and 2 below:

TABLE 1

0.6 mg

Speed: 197600 tab/hr which is 27 rpm

| Force (KN) | Weight (mg) | Weight RSD | Thickness (mm) | Hardness (Kp) | Hardness range | DT | Friability |
|---|---|---|---|---|---|---|---|
| 5.5 | 500.58 | 0.58 | 4.95 | 5.88 | 5.7-6.1 | 30 s | |
| 6 | 504.15 | 0.89 | 4.86 | 6.79 | 5.7-7.7 | 40 s | 0.73 |
| 7.1 | 503.68 | 1.01 | 4.6 | 9.41 | 8.3-10.4 | 2 m 30 s- 2 m 15 s | 0.25 |
| 8 | 499.68 | 0.69 | 4.52 | 10.24 | 9.8-10.9 | 3 m 40 s- 5 m 35 s | 0.52 |
| 8.5 | 502.04 | 0.93 | 4.47 | 11.7 | 11.2-12.8 | 4 m 30 s- 5 m 46 s | 0.25 |
| 9 | 505.74 | 0.62 | 4.43 | 12 | 11.7-12.6 | 6 m 15 s- 7 m 55 s | 0.14 |
| 10.2 | 504.8 | 0.57 | 4.31 | 13.74 | 12.8-14.6 | 7 m 19 s- 8 m 8 s | |

TABLE 2

0.8 mg

Speed: 329400 tab/hr
which is 45 rpm

| Force (KN) | Weight (mg) | Weight RSD | Thickness (mm) | Hardness (Kp) | Hardness range | DT | Friability |
|---|---|---|---|---|---|---|---|
| 5.1 | 497.01 | 0.67 | 4.88 | 2.94 | 2.4-3.1 | 20 s | 1.1 (severe chipping) |
| 6.4 | 497.97 | 0.75 | 4.66 | 4.22 | 3.7-4.7 | 30-35 s | 0.38 (slight chipping) |
| 7 | 499.49 | 1 | 4.5 | 5.26 | 4.6-6.0 | 1 m 10 s | 0.44 |
| 8 | 496.66 | 0.57 | 4.43 | 6.51 | 6.0-7.1 | 2 m 42 s | 0.14 |
| 9.1 | 497.56 | 0.55 | 4.31 | 7.87 | 7.5-8.3 | 2 m 35 s- 3 m 59 s | 0.1 |
| 10 | 503.16 | 0.71 | 4.25 | 8.34 | 8-8.9 | 3 m 40 s- 4 m 30 s | 0.05 |
| 11.2 | 503.21 | 0.66 | 4.18 | 9.65 | 9.3-10.1 | 5 m 40 s- 6 m 55 s | 0.03 |
| 12.1 | 502.76 | 0.39 | 4.05 | 11-5 | 10.9-11.8 | 8 m 34 s | |

Figure 1:
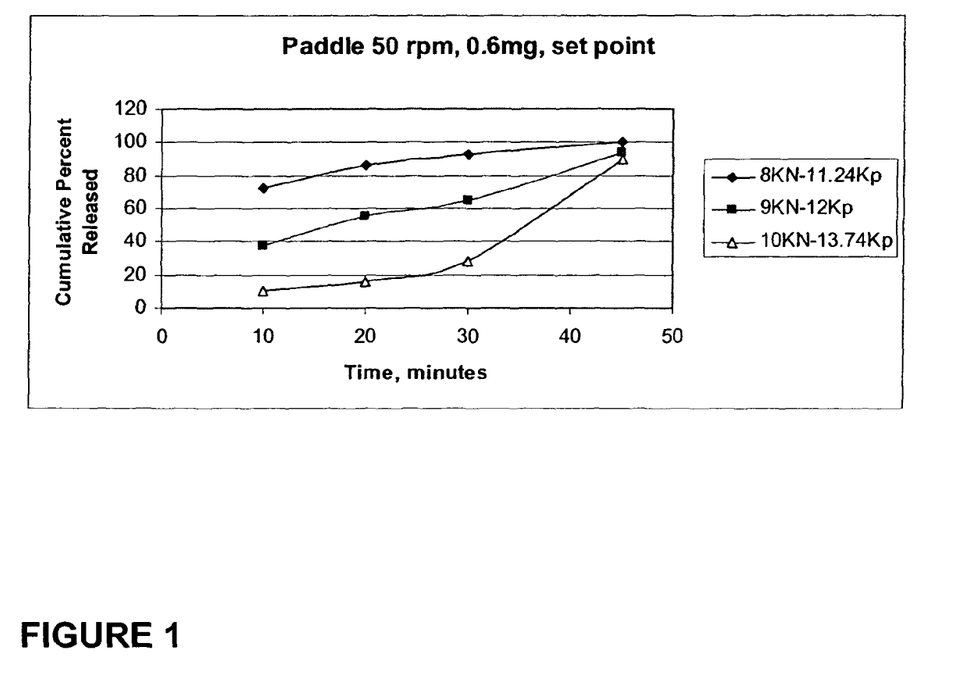
FIG. 1 shows the dissolufion profile for tablets prepared using different compression forces.

Where:
RSD is Relative Standard Deviation; and
DT is disintegration time
and their dissolution profiles are outlined in FIG. 1 below:

Example 4

Induction and Assessment of Arthritis

Arthritis induced in rodents by the systemic administration of type II collagen (CII) is an experimental model with many resemblances to RA, and is widely used for studying the disease processes (reviewed in Wooley P H, Chapedelaine J M. Immunogenetics of collagen-induced arthritis. *Crit Rev Immunol* 1987; 8: 1-22; and Trentham D E. Collagen arthritis as a relevant model for rheumatoid arthritis. *Arth Rheum* 1982; 25: 9116).

Upon immunization with purified CII in complete Freund's adjuvant, genetically susceptible strains of rodents develop arthritis, which is characterized by cellular and humoral immune responses to CII. Like RA, collagen-induced arthritis (CIA) is characterized by the rapid onset of inflammation of joints followed by the erosion of cartilage and bone.

Highly purified bovine CIA type II collagen can be obtained from Chondrex, Inc., 2607 151st Place NE, Redmond, Wash. 98052, USA Animals (Male Lewis rats or Male DBA/1 J mice (H-2$^q$) (Harlan Laboratories UK, Oxford, UK) are injected intradermally at the base of their tails with a single injection of 100 µg of CII, emulsified in complete Freund's adjuvant (Difco, Detroit, Mich., USA) at 8-10 weeks of age.

Animals are monitored for signs of arthritis one week post immunization on a daily basis and a clinical scoring system is adopted wherein each limb is given a clinical score on the basis of visual signs of oedema and/or erythema as follows: 0=normal, 1=slight swelling and/or erythema at the base of the paw, 2=frank oedema and erythema involving the entire paw, 2·5=pronounced oedema and erythema leading to an incapacitated limb mobility, 3=ankylosis, as previously described in Malfait A M, Butler D M, Presky D H et al., Blockade of IL-12 during the induction of collagen-induced arthritis (CIA) markedly attenuates the severity of the arthritis. *Clin Exp Immunol* 1998; 111: 377-83.

Each limb is graded in this way, giving a maximum possible score of 12 per animal. The hind paws are also measured daily, for paw swelling with the help of a caliper (least detectable change=0·1 mm, Kroeplin, Schluchtern, Germany).

In the present study, rheumatoid Arthritis was induced in the Collagen Induced Arthritis model (CIA-model) in lewis rats (8-9 weeks), by intradermal injection of porcine collagen type II.

In the non-treated collagen-injected group (CIA-group) disease occurred from day 11-14.

In the treatment group rats were treated twice daily with either 50 mg/kg 5-CNAC, 50 mg/kg 5-CNAC+calcitonin 2 mg/kg.

Figure 2:
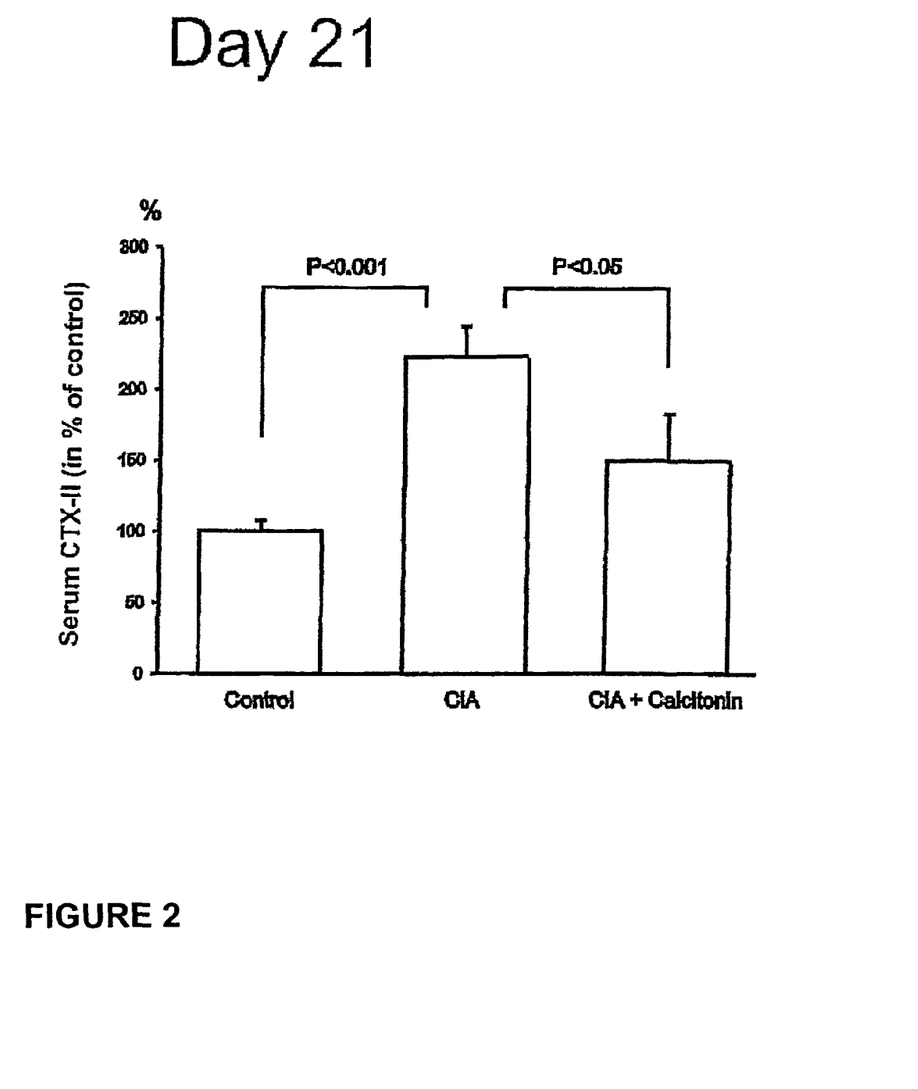
FIG. 2 shows serum c-terminal telopeptide of type II collagen (serum CTX-II) in % of control on day 21 after collagen injecton for the different groups: control, Collagen Induced Arthntis model (CIA) and CIA + Calcitonin.

Results are shown in FIG. 2, where serum c-terminal telopeptide of type II collagen (serum CTX-II) in % of control on day 21 after collagen injection is shown for the different groups (control, CIA and CIA+Calcitonin).

Disease was detected in the CIA-group by a significant increase in serum c-terminal telopeptide of type II collagen (serum CTX-II) compared to control. Treatment with Calcitonin was able to reduce this by 33%.

The invention claimed is:

1. A method of treating rheumatoid arthritis in a patient in need thereof comprising orally administering to a patient having rheumatoid arthritis a therapeutically effective amount of a calcitonin in free or salt form and a delivery agent for calcitonin, wherein the delivery agent is selected from the group consisting of N-(5-chlorosalicyloyl)-8-aminocaprylic acid (5-CNAC), N-(10-[2-hydroxybenzoyl]amino)decanoic acid (SNAD), N-(8-[2-hydroxybenzoyl]amino)caprylic acid (SNAC) and pharmaceutically acceptable salts, hydrates and alcohol solvates thereof, wherein said calcitonin in free or salt form is provided to said patient in a dosage range of between 0.4 mg and 2.5 mg.

2. A method for reducing inflammation of the joints associated with rheumatoid arthritis in a patient in need thereof comprising orally administering to a patient having rheumatoid arthritis a therapeutically effective amount of a calcitonin in free or salt form and a delivery agent for calcitonin, wherein the delivery agent is selected from the group consisting of N-(5-chlorosalicyloyl)-8-aminocaprylic acid (5-CNAC), N-(10-[2-hydroxybenzoyl]amino)decanoic acid (SNAD), N-(8-[2-hydroxybenzoyl]amino)caprylic acid (SNAC) and pharmaceutically acceptable salts, hydrates and alcohol solvates thereof, wherein said calcitonin in free or salt form is provided to said patient in a dosage range of between 0.4 mg and 2.5 mg.

3. A method for reducing swelling of skeletal joints associated with rheumatoid arthritis in a patient in need thereof comprising orally administering to a patient having rheumatoid arthritis a therapeutically effective amount of a calcitonin in free or salt form and a delivery agent for calcitonin, wherein the delivery agent is selected from the group consisting of N-(5-chlorosalicyloyl)-8-aminocaprylic acid (5-CNAC), N-(10-[2-hydroxybenzoly]amino)decanoic acid (SNAD), N-(8-[2-hydroxybenzoyl]amino)caprylic acid (SNAC) and pharmaceutically acceptable salts, hydrates and alcohol solvates thereof, wherein said calcitonin in free or salt form is provided to said patient in a dosage range of between 0.4 mg and 2.5 mg.

4. A method for decreasing pain associated with rheumatoid arthritis in a patient in need thereof comprising administering orally to a patient having rheumatoid arthritis a therapeutically effective amount of a calcitonin in free or salt form and a delivery agent for calcitonin, wherein the delivery agent is selected from the group consisting of N-(5-chlorosalicyloyl)-8-aminocaprylic acid (5-CNAC), N-(10-[2-hydroxybenzoly]amino)decanoic acid (SNAD), N-(8-[2-hydroxybenzoyl]amino)caprylic acid (SNAC) and pharmaceutically acceptable salts, hydrates and alcohol solvates thereof, wherein said calcitonin in free or salt form is provided to said patient in a dosage range of between 0.4 mg and 2.5 mg.

5. The method according to claim 1, wherein said calcitonin is salmon calcitonin.

6. The method according to claim 1, wherein the delivery agent is a disodium salt, an alcohol solvate or a hydrate of a compound of formula I.

7. The method according to claim 1, wherein said pharmaceutical composition comprises a delivery agent selected from the group consisting of a disodium salt of 5-CNAC, a disodium salt of SNAD, and a disodium salt of SNAC.

8. The method according to claim 1 wherein said pharmaceutical composition comprises a delivery agent in micronized form.

9. The method according to claim 8 wherein said micronized delivery agent has an average particle size of less than 10 micrometers.

10. The method according to claim 1, wherein the dosage range is between 0.6 mg and 1.2 mg.

11. The method according to claim 1, wherein said dose is administered once per day.

12. The method according to claim 1, wherein said dose is administered twice a day.

* * * * *